United States Patent [19]

Khanna et al.

[11] Patent Number: 4,990,636

[45] Date of Patent: Feb. 5, 1991

[54] PROCESS FOR THE PRODUCTION OF ALPHA-6-DEOXYTETRACYCLINES AND HYDROGENATION CATALYST USEFUL THEREIN

[75] Inventors: Jagmohan Khanna; Kiran Bala; Inder P. S. Grover, all of New Delhi, India

[73] Assignee: Ranbaxy Laboratories Limited, India

[21] Appl. No.: 477,571

[22] Filed: Feb. 9, 1990

Related U.S. Application Data

[62] Division of Ser. No. 263,721, Oct. 28, 1988, Pat. No. 4,902,447.

[51] Int. Cl.$^5$ .......................... C07F 15/00; C07F 9/00
[52] U.S. Cl. ........................................ 556/23; 556/13; 552/207; 552/203
[58] Field of Search ........................ 556/23, 13

[56] References Cited

PUBLICATIONS

Dulcetti, G.; Hoffman, N. W.; Collman, J. P., "Oxidative-Addition Reactions of 10 Nitrosyl Complexes", Inorganica Chimica Acta, vol. 6, No. 4, (1972), pp. 531–542.

K. K. Pandey and U. C. Agarwala, "Reaction of Nitrosyl Chloride Nitrosyl Bromide with Monochlorotris(-Triphenylphosphine)Rhodium(I)," Indian J. Chem., vol. 19A, No. 8, (Aug. 1980), pp. 805–807.

*Primary Examiner*—Howard T. Mars
*Assistant Examiner*—Porfirio Nazario-Gonzalez
*Attorney, Agent, or Firm*—Bryan, Cave, McPheeters & McRoberts

[57] ABSTRACT

A coordination compound useful as a hydrogenation catalyst, having the formula:

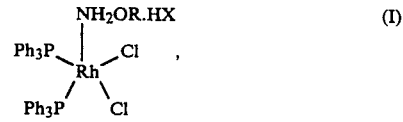

wherein Ph is phenyl; R is hydrogen or $C_1$–$C_4$ alkyl; and X is chloro, bromo or iodo. This compound is particularly useful as a homogeneous hydrogenation catalyst in the production of alpha-6-deoxytetracyclines, particularly the antibiotic doxycycline. The desired alpha-6-deoxy product is produced in high yields and stereospecificities, the process requiring the use of minimal quantities of rhodium metal in the hydrogenation catalyst per mole of the 6-methylenetetracycline hydrogenated.

6 Claims, No Drawings

PROCESS FOR THE PRODUCTION OF ALPHA-6-DEOXYTETRACYCLINES AND HYDROGENATION CATALYST USEFUL THEREIN

This is a divisional, of U.S. Application Ser. No. 07/263,721, filed Oct. 28, 1988, Pat. No. 4,902,447.

This invention relates to a process for the preparation of alpha-6-deoxytetracyclines and a hydrogenation catalyst useful therein, and more particularly to such a process and catalyst useful in the production of the antibiotic doxycycline, viz., alpha-6-deoxy-5-oxytetracycline.

BACKGROUND OF THE INVENTION

The preparation of doxycycline and other alpha-6-deoxytetracyclines was first described in Blackwood et al. U.S. Pat. No. 3,200,149 granted Aug. 10, 1965. That patent described their preparation by the catalytic hydrogenation of a corresponding 6-methylene intermediate, e.g., in the case of doxycycline, 11a-chloro-6-deoxy-6-demethyl-6-methylene-5-oxytetracycline (11a-chloro methacycline) or 6-deoxy-6-demethyl-6-methylene-5-oxytetracycline (methacycline), in the presence of a heterogeneous noble metal catalyst, e.g. palladium on carbon. The Blackwood patent disclosed the production, in yields of up to about 50%, of equimolar proportions of the diastereoisomers (epimers) of the 6-deoxytetracyclines. In the case of doxycycline, the patent disclosed the co-production of the corresponding beta epimer, beta-6-deoxy-5-oxytetracycline.

Subsequent efforts have been directed to the development of syntheses for producing the 6-deoxytetracyclines in greater yields and with greater stereoselectivity of formation of the desired alpha epimers, e.g., doxycycline. Thus, Korst U.S. Pat. No. 3,444,198 granted May 13, 1969, disclosed that the stereoselectivity of formation of the alpha epimers may be increased when the noble metal hydrogenation catalyst is poisoned. The Korst patent described the formation of epimeric mixtures of the 6-deoxytetracyclines in total yields of up to about 60%, with the stereoselective production of the alpha epimers in amounts of up to about 90% of the epimeric product mixtures. The use of other noble metal or noble metal salt compositions as heterogeneous hydrogenation catalysts in the production of doxycycline has also been disclosed in the literature. See, for example, Morris U.S. Pat. No. 3,954,862 granted May 4, 1976 and Faubl et al U.S. Pat. No. 3,962,131 granted June 8, 1976.

The use of rhodium halide complexes containing tertiary phosphine ligands, e.g., tris (triphenylphosphine) chloro rhodium (I), as homogeneous hydrogenation catalysts was first described by Wilkinson et al. in 1966 J. Chem. Soc. 1711–32. Subsequently, a number of soluble complexes of platinum metals, particularly rhodium, with halides and tertiary phosphines or the like, have been described as useful in a variety of regiospecific, stereoselective and asymmetric reduction reactions. See Knowles et al., Chem. Communs. 1445 (1968); Horner et al., Angew Chem. Int. Ed. 7, 942 (1968); Vol Pin et al., Russian Chemical Reviews, 38, 273–289 (1969); Augustine et al., Ann. N.Y. Sci., 158, 482–91 (1969); Ruesch et al., Tetrahedron, 25, 807–11 (1969); Piers et al., Chem. Communs. 1069–70 (1969); "Aspects Of Homogeneous Catalysis", Vol. I, pp. 5–75 (1970), Carlo Manfredi, Milan, Italy; "Homogeneous Catalysis, Industrial Applications And Implications," Vol. 70, Advances in Chemistry Series, American Chemical Society; Grubbs et al., J. Am. Chem. Soc., 93, 3062 (1971); Kagan et al., J. Am. Chem. Soc., 94, 6429 (1972); Knowles et al., Chem. Communs. 10 (1972); and Harmon et al., Chem. Rev. 73, 21–52 (1973). Similar disclosures have been made in the patent literature. See, for example, U.S. Pat. Nos. 3,489,786; 3,549,780; and 3,639,439; and British Pat. Nos. 1,121,642; 1,121,643; 1,138,601; and 1,219,763.

The use of rhodium chloride/triphenylphosphine and similar complexes as homogeneous, stereospecific hydrogenation catalysts in the production of doxycycline and other alpha-6-deoxy-5-oxytetracyclines has also been extensively discussed in the patent literature. See, for example, U.S. Pat. Nos. 3,907,890; 3,962,331; 4,001,321; 4,207,258; 4,550,096; 4,743,699; and French Pat. No. 2,216,268.

The present invention is directed to an improved process for the production of doxycycline and other alpha-6-deoxytetracyclines, and a homogeneous catalyst useful therein, wherein the desired alpha epimer is produced in both high yield and stereospecificity, and the noble metal constituent of the hydrogenation catalyst is utilized in smaller proportions than heretofore required and is readily recoverable from the reaction mixture for re-use. Other objects and advantages of this invention will be apparent from the following description of preferred embodiments thereof.

SUMMARY OF THE INVENTION

This invention comprises an improved process for the preparation of alpha-6-deoxy-tetracyclines by the hydrogenation of the corresponding 6-methylenetetracyclines, in the presence of a new type of homogeneous rhodium coordination compound catalyst. In particular, the rhodium coordination compound has the formula:

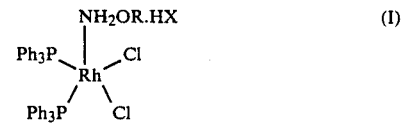

wherein
Ph is phenyl;
R is hydrogen or $C_1$–$C_4$ alkyl; and
X is chloro, bromo or iodo.

Elemental and infra-red analyses of specific examples of the catalyst of the invention are set forth in Table III below. As indicated therein, such analyses are consistent with the above formula. The formula has not yet been confirmed by x-ray analysis.

In accordance with the present invention it has been found that when an appropriate 6-methylenetetracycline substrate is hydrogenated in the presence of a homogeneous catalyst of the preceding type, the corresponding alpha-6-deoxytetracycline is produced in greater than about 95% yield and without the co-production of substantial amounts of the corresponding beta-6-deoxytetracycline epimer. Further, the hydrogenation may be carried out in the presence of substantially smaller quantities of rhodium than required in previously described homogeneous catalyses for the production of doxycycline or other alpha-6-deoxytetracyclines.

The novel hydrogenation catalyst of the present invention thus facilitates the production of doxycycline or the like in high yields and purities, and provides increased economies of operation, both because of the decreased quantities of rhodium required for catalysis and because of the elimination of expensive purification operations heretofore required for separation of the undesired beta epimers.

PREFERRED EMBODIMENTS OF THE INVENTION

The catalysts of the invention are preferably prepared by reacting a rhodium complex, desirably tris(triphenylphosphine) chloro rhodium (I), with an hydroxylamine salt, preferably hydroxylamine hydrochloride or its O-alkyl derivative. The hydroxylamine thus reacted has the general formula $NH_2OR \cdot HX$, wherein R and X are as defined hereinabove. In the preferred hydroxylamine, hydroxylamine hydrochloride, R is H and X is Cl.

The hydroxylamine hydrochloride is normally reacted in excess, e.g., in an amount of about 2 to 10 moles/mole of the rhodium coordination compound reactant. The reaction is carried out in solution, in a reaction-inert solvent, preferably methanol, ethanol, n-propanol, i-propanol or other water miscible polar solvent. The solvent is degassed with nitrogen prior to use.

The hydroxylamine-rhodium compound reaction is carried out at reaction temperatures in the range of from about 10° to 75° C., preferably under ambient conditions (20°–25° C.). The reaction can be followed visually through color changes of the reaction mixture from an initial purple color to a yellow/orange color. The time of the reaction is about 3 to 30 hours. The use of a nitrogen atmosphere during the reaction is preferred. The catalysts are recovered from the reaction mixture by conventional methods.

Alternatively, the catalyst can be prepared from a rhodium salt, preferably rhodium chloride; a hydroxylamine salt or its O-alkyl derivative, preferably hydroxylamine hydrochloride; and a tertiary phosphine, preferably triphenylphosphine, in a degassed lower alcohol, preferably ethanol. Hydroxyamine salts which may be thus reacted have the formula $NH_2OR \cdot HX$, wherein R and X are as defined above.

The hydroxylamine hydrochloride and triphenylphosphine reagents are generally reacted in excess, preferably in an amount of about 2 to 6 moles each, per mole of the rhodium salt reactant. The reaction medium is chosen from lower alcohols such as methanol, ethanol, n-propanol, i-propanol or butanol, degassed with nitrogen. The reaction is carried out at temperatures of from about 10° to 100° C., preferably initially at an elevated temperature (desirably about 78° C.), followed by further reaction under ambient conditions (about 20°–25° C.). The total reaction time is about 3 to 30 hours, preferably about 24 hours. The use of a nitrogen atmosphere is required.

As thus prepared, the catalyst is usually insoluble in the reaction medium and may be recovered by conventional means, e.g., by filtration, washing with the solvent used for the reaction, and drying at room temperature under reduced pressure. The rhodium remaining in the mother liquor can be recovered by conventional methods and recycled. Alternatively, the catalyst may be prepared and utilized in hydrogenation reactions without isolation from the reaction medium in which it is formed.

In accordance with a further feature of the invention, the hydrogenation catalyst is utilized in the production of any of the known alpha-6-deoxytetracyclines, preferably those having the formula:

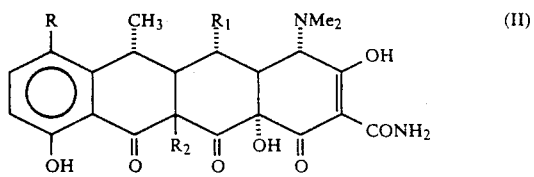

wherein R and $R_2$ are each hydrogen or chloro, and $R_1$ is hydrogen or hydroxyl.

The preceding compounds are produced by hydrogenation of the corresponding 6-methylenetetracycline compounds of the formula:

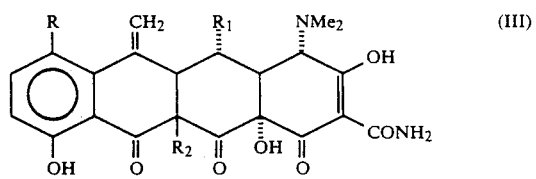

wherein R, $R_1$ and $R_2$ are as defined above.

6-methylenetetracyclines which are thus reacted may be prepared in the manner known in the art, e.g., as described in Blackwood U.S. Pat. No. 2,984,986 granted May 16, 1961 or Villax U.S. Pat. No. 3,848,491 granted Nov. 19, 1974.

Preferably, the catalytic hydrogenation is utilized to prepare doxycycline (wherein R is hydrogen and $R_1$ is hydroxyl) from 11a-chloro methacycline (wherein R is hydrogen, $R_1$ is hydroxyl, and $R_2$ is chloro).

The hydrogenation reaction is carried out in the manner known in the art, with the stereospecific formation of the desired alpha epimer in yields in excess of 95%. HPLC analyses of the hydrogenation products indicate beta-epimer contents of less than 0.5%. The hydrogenation is effected in the presence of from about 0.4 to 1.5 millimoles of catalyst per mole of 6-methylenetetracycline reacted. The amount of rhodium required for reduction varies from about ½ to 1/100th that required in previously described processes. Accordingly, the catalytic hydrogenation of the present invention provides superior yields and purities of the desired alpha-6-deoxytetracyclines, with substantially improved efficiencies in the operation.

The reaction is suitably carried out in a lower alkanolic solvent, preferably methanol, ethanol, propan-1-ol, propan-2-ol, or butanol. The solvents are degassed with nitrogen prior to use.

The reaction time depends on the amount of catalyst and the type of autoclave used for hydrogenation. Normally, to obtain high yields and purities, reaction times of from about 3 to 16 hours are utilized. It is preferred, but not critical, to carry out the reaction under pressures ranging from about 3 to 12 $kg/cm^2$, and at temperatures of from about 50° to 90° C. At temperatures lower than about 50° C. the reaction is too slow, and at higher temperatures decomposition occurs.

A small amount of triphenylphosphine, e.g., from about 30 to 60 millimoles per mole of the 6-methylenetetracycline substrate, when added to the reaction mixture prior to hydrogenation, acts as a promoter and accelerates the rate of hydrogen absorption, thus facilitating completion of the reaction. The optimum quantity of triphenylphosphine for a given catalyst is determined empirically.

The doxycycline or other alpha-epimer is crystallized as an acid addition salt from the reaction mixture, preferably in the form of the sulfosalicylate salt (by adding excess sulfosalicylic acid). The purity is more than 99.5% by HPLC. The doxycycline sulfosalicylate is thereafter converted directly to doxycycline hyclate (the hemiethanolate hemihydrate) in stoichiometric yield by procedures known in the art.

The catalytic hydrogenation may be utilized in a single step to effect both the reductive dehalogenation and reduction of the 6-methylene group of an 11a-halo-6-deoxy-6-demethyl-6-methylenetetracycline, e.g., 11a-chloro methacycline. The corresponding alpha-6-deoxytetracycline, e.g., doxycycline, is directly produced in improved yield and purity, and with decreased rhodium consumption.

In a preferred embodiment, a mixture containing an 11a-halo-6-deoxy-6-demethyl-6-methylenetetracycline, preferably the p-toluene sulfonate of 11a-chloro methacycline; bis(triphenylphosphine)(hydroxylamine hydrochloride) dichloro rhodium (II) or its O-alkyl derivative complex, preferably hydroxylamine hydrochloride complex; and a tertiary phosphine, preferably triphenylphosphine, in methanol is subjected to agitation in a stainless steel autoclave, and hydrogenated at about 50° to 90° C. under a pressure between about 3 and 12 kg/cm$^2$, prior to the termination of the reaction. Sulfosalicylic acid is added and the reaction mixture is cooled to about 0° C. for 2–4 hours. The alpha-6-deoxy-5-oxytetracyline sulfosalicylate, preferably doxycyline sulfosalicylate (or toluene sulfonate) thus obtained is filtered and washed with methanol.

Alternatively, the reductive dehalogenation and hydrogenation can be carried out with a two-step process initially effecting 11a-dehalogenation with a conventional catalyst, e.g., 5% Rh/C or 5% Pd/C in methanol. The initial catalyst is then removed by filtration, and the solution is again subjected to hydrogenation in the presence of the bis(triphenylphosphine) (hydroxylamine hydrochloride) dichloro rhodium (II) or other catalyst.

In the following examples, particularly preferred embodiments of the hydrogenation catalyst and the process for the preparation of alpha-6-deoxytetracyclines therewith are described. In the examples, all temperatures are given in Degrees Celsius and all parts and percentages by weight, unless otherwise specified.

EXAMPLE 1

Preparation of Bis(Triphenylphosphine) (Hydroxylamine Hydrochloride) Dichloro Rhodium (II) Catalyst To a well stirred suspension of tris(triphenylphosphine) chloro rhodium (I) (2 g, 2.16 mM) in ethyl alcohol (20 ml) was added a solution of hydroxylamine hydrochloride (0.33 g, 4.75 mM) in ethyl alcohol (40 ml). The reaction mixture was stirred at 20°–25° C. under a nitrogen atmosphere for 24 hrs. As the reaction progressed, the color of the mixture changed from purple to orange. The solid was filtered, washed with ethyl alcohol, and dried under reduced pressure at room temperature to yield 1.48 g (89%) of an orange product, m.p. 230°–32° C.

EXAMPLE 2

Production of Doxycycline from Methacycline Hydrochloride with Bis (Triphenylphosphine) (Hydroxylamine Hydrochloride) Dichloro Rhodium (II) Catalyst 6-deoxy-6-demethyl-6-methylene-5-oxytetracycline hydrochloride (20g, 0.042 mole), 0.033 g of the catalyst prepared as described in Example 1, and methanol (240 ml) were charged to a hydrogenation vessel The reactants were hydrogenated at 85° C. and at a pressure of 80–90 psi for 7 hrs. Sulfosalicylic acid (32 g, 0.127 mole) was added to the reaction mixture, and the mixture was stirred for 3 hrs. at room temperature. Doxycycline sulfosalicylate (SSA) separated out immediately and was then filtered, washed first with water (100 ml), and then with methanol:water (1:1) (100 ml), and dried at 55°–60° C. The resulting product weighed 27.5 g (99.4%) HPLC analysis showed: alpha isomer 99.8%, beta isomer 0.05%, methacycline 0.05%, and others 0.1%.

The doxycycline SSA obtained above was dissolved in hot 20% ethanolic-HCl (250 ml) and treated with activated charcoal (1.25 g) for 15 minutes. The reaction mixture was filtered through a G-4 sintered funnel. Concentrated hydrochloric acid (20 ml) was added to the filtrate, and the mixture was agitated at 55°–60° C. for 3 hrs. It was cooled to 40° C., filtered, washed with acetone (100 ml), and dried. The resulting doxycycline hyclate weighed 16.47 g (77.3%). From the mother liquor, a second crop was recovered as doxycycline SSA (5.0 g).

Similarly, the p-toluene sulfonate (PTS) of doxycycline was obtained when the sulfosalicylic acid was replaced by p-toluene sulfonic acid.

The yield, stereospecificity, and purity of the product obtained in Example 2 are compared with those claimed in corresponding examples of various prior art doxycycline synthesis patents in the following tabulation:

TABLE I

Comparison of Doxycycline Produced in Example 2 With Prior Art Products

| Patent No. MOT | Example | Rhodium used per kg of MOT.HCl (mg) | Yield$^d$(%) | Content (%) Alpha Isomer | Beta Isomer | MOT | Purity of isolated product (%) |
|---|---|---|---|---|---|---|---|
| U.S. Pat. No. 4,207,258 | 2 | 19540 | 78.0 | NS | NS | NS | 99.3$^b$ |
| French 12,216,268 | 3 | 21252 | 90.6 | NS | NS | NS | NS |
| U.S. Pat. No. 3,954,862 | 3 | 1962 | 80.0 | 81.0* | 1.6* | NS | NS$^a$ |
| U.S. Pat. No. 4,001,321 | 1 | 9369 | 95.0 | 93.0 | 2.0–3.0* | NS | 93.0$^b$ |
| U.S. Pat. No. 3,962,131 | 2 | less than 3332.4 | 98.8 | NS | NS | NS | 99.7$^b$ |
| U.S. Pat. No. 3,907,890 | 5 | 0 | 75.2 | 98.0 | 2.0 | 0 | 98.0$^a$ |

TABLE I-continued

Comparison of Doxycycline Produced in Example 2 With Prior Art Products

| Patent No. MOT | Example | Rhodium used per kg of MOT.HCl (mg) | Yield[d](%) | Content (%) Alpha Isomer | Content (%) Beta Isomer | MOT | Purity of isolated product (%) |
|---|---|---|---|---|---|---|---|
| Re. 32,535 | 4 | 620.6 | 99.1 | 99.89 | 0 | 0 | 99.89[c] |
| Present Invention | 2 | 221 | 99.4 | 99.8 | 0.05 | 0.05 | 99.8[a] |

*Values in the reaction mixture
NS: Not stated
MOT: 6-deoxy-6-demethyl-6-methylene-5-oxytetracycline (methacycline).
[a]HPLC analysis
[b]UV analysis
[c]Paper chromatography
[d]Examples with highest yields considered for comparison purposes.

From the preceding table it will be seen that the only prior art processes which resulted in the formation of doxycycline products in yields, stereospecificities, and purities which even approached those obtained in Example 2 (the processes of U.S. Pat. No. 3,962,131 and Re. 32,535), required from three to as much as sixteen times the amount of rhodium utilized in Example 2. Use of the procedure of Example 2 thus provides substantially and unexpectedly superior economies relative to each of the noted prior art procedures.

EXAMPLE 3

Example 2, when repeated with 0.028 g of the catalyst prepared as described in Example 1, yielded doxycycline sulfosalicylate (26.40 g, 95.4%). The quality of the product was comparable to that obtained in Example 2.

EXAMPLE 4

Example 2 was repeated in the presence of 0.5 g of triphenylphosphine. The reaction was completed in 5 hrs. Doxycycline sulfosalicylate was produced in an amount of 27.3 g (98.7%); the reaction product contained (by HPLC): alpha isomer 99.83%, beta isomer 0.09%, methacycline none, and other impurities 0.1%.

EXAMPLE 5

Production of Doxycycline from 11a-Chloro Methacycline PTS Salt With Bis (Triphenylphosphine) (Hydroxylamine Hydrochloride) Dichloro Rhodium (II) Catalyst 11a-chloro-6-demethyl-6-deoxy-6-methylene-5-oxytetracycline p-toluene sulfonate (100 g, 0.154 mole), triphenylphosphine (46 g, 0.175 mole), and 0.15 g of the catalyst of Example 1 were dissolved in methanol (600 ml) in a stainless steel pressure vessel. The reactor was flushed with nitrogen thoroughly before adding hydrogen to it. The reaction mixture was thoroughly hydrogenated for 7 hrs at 80°–85° C. and at a pressure of 90–95 psi.

Sulphosalicylic acid was added and doxycycline SSA salt was isolated in the same manner that the SSA salt was recovered in Example 2 (93.5 g, 91.9%) and converted to its hyclate, yielding (in two crops) 61.0 g (96.6%) of total product. No beta isomer or methacycline was detectable by thin layer chromatography. From the mother liquor, a second crop obtained as doxycycline SSA, weighed 12.0 g. HPLC analysis: alpha epimer 99.8%, beta epimer 0.07%, methacycline none, and others 0.1%.

The yield, stereospecificity, and purity of the product obtained in Example 5 are compared with those claimed in corresponding examples of various prior art doxycycline synthesis patents in the following tabulation:

TABLE II

Comparison of Doxycyline Produced in Example 5 With Prior Art Products

| Patent No. | Example | Rhodium used per kg of 11a-Cl MOT (mg) | Yield[d] (%) | Content (%) alpha isomer | Content (%) beta isomer | MOT | Purity of isolated product (%) |
|---|---|---|---|---|---|---|---|
| U.S. Pat. No. 3,962,331 | 1 | 4889 | 70.1 | 95.0* | 5.0* | Slight traces | 98.9 |
| U.S. Pat. No. 3,954,862 | 17 | 2140 | 86.7 | 59.9 | 1.33 | 0.8 | 59.0[a] |
| Re. 32,535 | 13 | 378.4 | 90.7 | 99.6 | 0.3 | 0 | 99.6[a] |
| Present Invention | 5 | 273 | 91.9 | 99.8 | 0.07 | NIL | 99.8[a] |

[a]HPLC analysis;
[b]UV analysis;
[c]Paper chromatography;
[d]Examples with highest yields considered for comparison purposes.
MOT: d-deoxy-6-demethyl-6-methylene-5-oxytetracycline (methacycline).
*In reaction mixture.

From the preceding table it will be seen that the only prior art process which resulted in the formation of a doxycycline product in a yield, stereospecificity, and purity which even approached the values obtained in Example 5 (the process of reissue patent Re. 32,535), required more than 35% more rhodium than employed in Example 5. Use of the procedure of Example 5 thus provides substantially and unexpectedly superior economies relative to the noted prior art process.

EXAMPLE 6

Example 5 was repeated, except that doxycycline was isolated as its PTS salt (85.7 g, 90.5%). Thin layer chromatography of the product showed only traces of methacycline and beta isomer.

EXAMPLE 7

Example 5 was again repeated, using ethanol (600 ml) as the solvent instead of methanol. Thin layer chromatography showed a major amount of doxycycline contaminated with only a negligible amount of methacycline, and no beta isomer.

EXAMPLE 8

Example 5 was repeated at 65°–70° C., while maintaining the other conditions constant. The product yield was relatively low (60 g, 58.9%). Thin layer chromatography of the product showed the presence of 2–3% methacycline.

EXAMPLE 9

Example 5 was again repeated, using 0.25 g rather than 0.15 g of the catalyst. The yield of doxycycline SSA was 93.7 g (92.1%). The purity of the product was comparable with that of Example 5.

EXAMPLE 10

Reductive Dehalogenation of 11a-Chloro Methacycline With Rh/C Catalyst, Followed by Preparation of Doxycycline With Bis (Triphenylphosphine) Hydroxylamine Hydrochloride) Dichloro Rhodium (II) Catalyst 11a-chloro-6-demethyl-6-deoxy-6-methylene-5-oxytetracycline p-toluenesulfonate (40g, 0.062 mole), and (50% wet) 5% Rh/C (1.0 g) in methanol (240 ml) were charged to a stainless steel hydrogenation vessel. The contents were hydrogenated at room temperature at a pressure of 0.5 kg/cm$^2$ until the absorption of hydrogen ceased (1 hr.). Thin layer chromatography of the reaction mixture showed almost pure methacycline. The Rh/C catalyst was separated by filtration.

The filtrate was charged back to the hydrogenator followed by the addition of 0.06 g of the catalyst prepared as described in Example 1, and triphenylphosphine (8.0 g, 0.03 mole). Hydrogenation performed under temperature and pressure conditions similar to those utilized in Example 2 gave doxycycline SSA (31.3 g, 76.9%). Doxycycline hyclate prepared from the sulfosalicylate in the same manner as described above contained negligible amounts of methacycline and beta isomer (by thin layer chromatography).

EXAMPLE 11

Preparation of Bis (Triphenylphosphine) (Hydroxylamine Hydrochloride) Dichloro Rhodium (II) Catalyst By Reaction of Rhodium Chloride, Hydroxylamine Hydrochloride, and Triphenylphosphine, and Production of Doxycycline Therefrom To a refluxing solution of triphenylphosphine (0.336 g, 1.28 mM) in ethyl alcohol (7.5 ml), was added a hot solution of rhodium trichloride trihydrate (0.060 g, 0.23 mM) in alcohol (2.5 ml). The refluxing was continued for 1 hr. under nitrogen. The reaction mixture was cooled to 20° C. and a solution of hydroxylamine hydrochloride (0.061 g, 0.87 mM) in ethanol (2 ml) was added thereto. The reaction mass was agitated at 20° C. for 20 hrs. The solid product thus formed changed from maroon to orange-yellow during the reaction.

The catalyst thus prepared was used without isolation in the hydrogenation of 11a-chloro-6-deoxy-6-demethyl-6-methylene-5-hydroxytetracycline PTS (100 g, 0.154 mole). The reaction was carried out in the manner described in Example 5, giving 92.9 g (91.3%) of doxycycline SSA. Thin layer chromatography showed a negligible amount of methacycline, and no beta isomer.

EXAMPLE 12

Preparation of Bis(Triphenylphosphine) (Methoxylamine Hydrochloride) Dichloro Rhodium (II) Catalyst A mixture of tris(triphenylphosphine) chlororhodium (I) (0.5 g, 0.54 mM) and methoxylamine hydrochloride (0.099g. 1.18 mM) in ethanol (15 ml) was stirred at 20° C. for 24 hrs. under a nitrogen atmosphere. The solid was filtered, washed thoroughly with ethanol, and dried under reduced pressure to give 0.384 g (90.8%) of an orange-colored product; m.pt. 165–67° C.

The same catalyst is prepared from rhodium chloride (0.15 g, 0.57 mM), triphenylphosphine (0.857 g, 3.27 mM) and methoxylamine hydrochloride (0.18 g, 2.15 mM), according to the procedure described in Example 11.

EXAMPLE 13

Production of Doxycycline from 11a-Chloro Methacycline PTS Salt With Bis (Triphenylphosphine) (Methoxylamine Hydrochloride) Dichloro Rhodium (II) Catalyst The hydrogenation of 11a-chloro-6-deoxy-6-demethyl-6-methylene-5-oxytetracycline p-toluenesulfonate was carried out as in Example 5, using 0.15g of the catalyst of Example 12. Doxycycline SSA was thus obtained in the amount of 91.8 g (90.2%). It contained traces of methacycline and beta isomer by thin layer chromatography.

EXAMPLE 14

Production of Doxycycline from Methacycline Hydrochloride with Bis (Triphenylphosphine) (Methoxylamine Hydrochloride) Dichloro Rhodium (II) Catalyst 0.15 g of the catalyst prepared as described in Example 12 was used for the hydrogenation of methacycline hydrochloride (100g) under the conditions of Example 2. Doxycycline SSA was formed in an amount of 135.0 g (98.0%). Thin layer chromatography showed only traces of methacycline and beta isomer.

EXAMPLE 15

Reductive Dehalogenation of 11a-Chloro Methacycline With Pd/C Catalyst, Followed by Preparation of Doxycycline With Bis (Triphenylphosphine) Methoxylamine Hydrochloride) Dichloro Rhodium (II) Catalyst 11a-chloro-6-deoxy-6-demethyl-6-methylene-5-oxytetracycline p-toluenesulfonate (40g, 0.06 mole) and 5% Pd/C (0.5g) were suspended in methanol (24% ml) in an autoclave. The contents were hydrogenated at a pressure of 0.5 kg/cm$^2$ at room temperature (30°–35° C.) until hydrogen absorption almost ceased (30 min.) Thin layer chromatography of the reaction mixture showed a major amount of methacycline.

The Pd/C catalyst was filtered off and the filtrate recharged to the hydrogenation vessel followed by the addition of the catalyst prepared as described in Example 12 (0.06 g), and triphenylphosphine (8.0 g, 0.03 mole). After flushing the reactor thoroughly with nitrogen, hydrogen was introduced at a pressure of 90-95 psi and hydrogenation carried out at 80°-85° C. for 7 hrs. Doxycycline SSA was isolated from the reaction mixture in the manner described above, in an amount of 32.2 g (79.1%).

EXAMPLE 16

Bis(Triphenylphosphine) (Ethoxylamine Hydrochloride) Dichloro Rhodium (II) Catalyst A solution of ethoxylamine hydrochloride (0.158 g, 1.62 mM) in ethyl alcohol (5 ml) was added to a suspension of tris (triphenylphosphine) chloro rhodium (I) (0.5 g, 0.54 mM) in ethanol (10 ml). The mixture was stirred at 20°-25° C. under nitrogen for 20 hrs. until the maroon particles of tris (triphenylphosphine) chloro rhodium (I) disappeared. The orange solid was filtered off, washed thoroughly with ethanol (2×5 ml) and dried at room temperature under vacuum to yield 0.394 g (91.5%) of orange product; m.pt. 154°-57° C.

EXAMPLE 17

Production of Doxycycline from 11a-Chloro Methacycline PTS Salt With Bis (Triphenylphosphine) (Ethoxylamine Hydrochloride) Dichloro Rhodium (II)-Catalyst 11a-chloro-6-deoxy-6-demethyl-6-methylene-5-oxyatetracycline p-toluene-sulfonate (100 g, 0.154 mole), and 0.150 g of the catalyst prepared as described in Example 16, in methanol, were hydrogenated as above (Example 5). Thin layer chromatography of the reaction mixture identified doxycycline as the major product with only a trace of methacycline present. On work-up, doxycycline SSA was obtained, 92.8 g (91.2%).

EXAMPLE 18

Production of Doxycycline from Methacycline Hydrochloride with Bis (Triphenylphosphine) (Ethoxylamine Hydrochloride) Dichloro Rhodium (II) Catalyst Methacycline hydrochloride (20 g, 0.042 mole) was subjected to hydrogenation with the catalyst of Example 16, employing the conditions of Example 2. Pure doxycycline was obtained and isolated as its PTS salt (24.9 g, 96.7%).

EXAMPLE 19

Preparation of Bis(Triphenylphosphine) (Isopropoxylamine Hydrochloride) Dichloro Rhodium (II) Catalyst A solution of isopropoxylamine hydrochloride (0.132 g, 1.18 mM) in ethanol (5 ml) was added to a suspension of tris (triphenylphosphine) chloro rhodium (I) (0.5 g, 0.54 mM) in ethanol (10 ml). The reaction was carried out employing the conditions given in Example 1. An orange colored product was obtained; yield 0.39 g (89%), m.pt. 168°-173° C.

EXAMPLE 20

Production of Doxycycline With Bis(Triphenylphosphine) (Isopropoxylamine Hydrochloride) Dichloro Rhodium (II) Catalyst The catalyst prepared as described in Example 19 was tested for its stereospecificity in the hydrogenation of methacycline and 11a-chloro methacycline under temperature and pressure conditions similar to those used in Examples 2 and 5, respectively. Doxycycline was obtained, only traces of methacycline and no beta isomer appearing upon analysis by thin layer chromatography.

EXAMPLE 21

Preparation of Bis(triphenylphosphine) (n-Propoxylamine Hydrochloride) Dichloro Rhodium (II) Catalyst The above catalyst was prepared in the same manner as described in Example 19, substituting n-propoxylamine hydrochloride for the isopropoxylamine hydrochloride reactant. Yield 0.392 g (89.6%), m.pt. 180°-187° C. This catalyst, when used for the hydrogenation of methacycline or 11a-chloro methacycline gave comparable results to those obtained in Examples 2 and 5, respectively.

The homogeneous catalysts prepared as described in Examples 1, 11, 16, 19 and 21 above, were analyzed and found to have the elemental analyses and infra-red absorption spectra set forth in Table III below:

TABLE III

ANALYSES OF HOMOGENEOUS CATALYSTS OF INVENTION

| Catalyst Prepared as Described in Example | C (%) | H (%) | N (%) | Cl (%) | Rh (%) | Characteristic infra-red absorption peak cm$^{-1}$ |
|---|---|---|---|---|---|---|
| 1 | 56.0 (56.3) | 4.4 (4.4) | 1.9 (1.8) | 13.6 (13.8) | 13.8 (13.4) | 3600(s,sh), 3280(s,sh), 730(sh), 3210(s,sh), 1620(s,sh), 680(sh), 510(sh, 340(s,sh) |
| 12 | 56.7 (56.8) | 4.4 (4.6) | 1.8 (1.8) | 13.6 (13.6) | 12.9 (13.2) | 3200(s,sh), 3160(s,sh), 1560(b), 740(sh), 690(sh), 510(sh), 340(s,sh) |
| 16 | 56.9 (57.3) | 4.5 (4.7) | 1.9 (1.7) | 13.1 (13.4) | 12.7 (12.9) | 3220(s,sh), 3160(s,sh), 1615(s,b), 1550(sh) 740(sh), 685(sh), 510(sh), 340(s,sh) |
| 19 | 57.4 (57.8) | 5.0 (4.9) | 1.7 (1.7) | 12.8 (13.1) | 12.6 (12.7) | 3230(s), 3200(s), 1640(b), 740(sh), 690(sh), 515(sh), 330(s,sh) |
| 21 | 57.6 (57.8) | 4.7 (4.9) | 1.8 (1.7) | 12.9 (13.1) | 12.5 (12.7) | 3230(s), 3190(s), 1635(b), 740(sh), 690(sh), 510(sh), |

TABLE III-continued

ANALYSES OF HOMOGENEOUS CATALYSTS OF INVENTION

| Catalyst Prepared as Described in Example | C (%) | H (%) | N (%) | Cl (%) | Rh (%) | Characteristic infra-red absorption peak cm$^{-1}$ |
|---|---|---|---|---|---|---|
| | | | | | | 340(s,sh) |

Calculated values are given in parenthesis
s = small, sh = sharp, b = broad.
Elemental analyses were done on Heraeus CHN-O-RAPID
Infra red absorption spectra were recorded on Pekin-Elmer 399-B It will be understood that various changes may be made in the procedures for preparing and utilizing the preferred catalyst embodiments described hereinabove without departing from the scope of the present invention. Accordingly, it is intended that the invention is not limited to the preceding description but should be construed in the light of the following claims:

We claim:

1. A coordination compound useful as a hydrogenation catalyst, and having the formula:

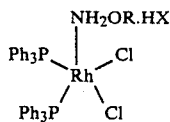 (I)

wherein

Ph is phenyl;
R is hydrogen or $C_1$–$C_4$ alkyl; and
X is chloro, bromo or iodo.

2. The compound of claim 1 wherein R is hydrogen, viz., bis(triphenylphosphine) (hydroxylamine hydrochloride) dichloro rhodium (II).

3. The compound of claim 1, wherein R is methyl, viz., bis(triphenylphosphine) (methoxylamine hydrochloride) dichloro rhodium (II).

4. The compound of claim 1, wherein R is ethyl, viz., bis(triphenylphosphine) (ethoxylamine hydrochloride) dichloro rhodium (II).

5. The compound of claim 1, wherein R is isopropyl, viz., bis(triphenylphosphine) (isopropoxylamine hydrochloride) dichloro rhodium (II).

6. The compound of claim 1, wherein R is n-propyl, viz., bis(triphenylphosphine) (n-propoxylamine hydrochloride) dichloro rhodium (II).

* * * * *